United States Patent
Wu et al.

(10) Patent No.: US 6,979,347 B1
(45) Date of Patent: Dec. 27, 2005

(54) IMPLANTABLE DRUG DELIVERY PROSTHESIS

(75) Inventors: Steven Z. Wu, Santa Clara, CA (US); Deborra Sanders-Millare, San Jose, CA (US); Sameer Harish, Fremont, CA (US); Ryan J. Santos, San Jose, CA (US); Li Chen, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/695,022

(22) Filed: Oct. 23, 2000

(51) Int. Cl.$^7$ .................................................. A61F 2/06
(52) U.S. Cl. .................... 623/1.15; 623/1.42; 623/1.43
(58) Field of Search .............................. 623/1.13, 1.15, 623/1.42, 1.43, 23.57, 23.75, 1.34, 1.44; 424/423

(56) References Cited

U.S. PATENT DOCUMENTS

| | | | | |
|---|---|---|---|---|
| 3,724,041 A | * | 4/1973 | Cleverley | 28/149 |
| 4,160,467 A | * | 7/1979 | Woodruff | 139/33 |
| 4,459,252 A | | 7/1984 | MacGregor | 264/46.9 |
| 5,059,211 A | | 10/1991 | Stack et al. | 606/198 |
| 5,163,952 A | | 11/1992 | Froix | 623/1 |
| 5,282,823 A | * | 2/1994 | Schwartz et al. | 623/1.22 |
| 5,306,286 A | | 4/1994 | Stack et al. | 606/198 |
| 5,342,348 A | * | 8/1994 | Kaplan | 604/891.1 |
| 5,425,739 A | | 6/1995 | Jessen | 606/155 |
| 5,464,650 A | | 11/1995 | Berg et al. | 427/2.3 |
| 5,527,337 A | | 6/1996 | Stack et al. | 606/198 |
| 5,605,696 A | | 2/1997 | Eury et al. | 424/423 |
| 5,629,077 A | * | 5/1997 | Turnlund et al. | 623/1.15 |
| 5,697,382 A | * | 12/1997 | Love et al. | 128/898 |
| 5,700,286 A | | 12/1997 | Tartaglia et al. | 623/1 |
| 5,713,949 A | | 2/1998 | Jayaraman | 623/1 |
| 5,722,984 A | * | 3/1998 | Fischell et al. | 606/198 |
| 5,766,710 A | | 6/1998 | Turnlund et al. | 428/36.1 |
| 5,769,883 A | * | 6/1998 | Buscemi et al. | 623/1.42 |
| 5,843,172 A | * | 12/1998 | Yan | 623/1.42 |
| 5,873,904 A | | 2/1999 | Ragheb et al. | 623/1 |
| 6,071,305 A | * | 6/2000 | Brown et al. | 623/1.43 |
| 6,120,536 A | | 9/2000 | Ding et al. | 623/1.43 |
| 6,120,847 A | | 9/2000 | Yang et al. | 427/335 |
| 6,206,915 B1 | | 3/2001 | Fagan et al. | 623/1.42 |
| 6,254,632 B1 | * | 7/2001 | Wu et al. | 623/1.15 |

(Continued)

FOREIGN PATENT DOCUMENTS

EP 0 850 651 A2 1/1998

(Continued)

OTHER PUBLICATIONS

Microtruder Technology Bulletin; www.randcastle.com; Mar. 14, 2000; 8 pages.

*Primary Examiner*—Paul B. Prebilic
(74) *Attorney, Agent, or Firm*—Squire, Sanders & Dempsey L.L.P.

(57) ABSTRACT

An apparatus and associated method for delivering a therapeutic substance to a vascular lumen, using an implantable prosthesis, such as a stent, which has grooves or trenches formed thereon. The grooves are formed on specific regions of the stent struts to increase the flexibility of the stent. The grooves also provide a therapeutic material carrying capability for treating intravascular ailments, such as instent restenosis and thrombosis. The therapeutic material loading of the grooves can be accomplished in several ways. For example, a pure therapeutic material or a pre-mixed material with a polymer solution, which enhances the adhesion properties of the material, may be deposited directly in to the grooves using conventional spray or modified dip techniques. In another example, a microextruded monofilament therapeutic material can be wound about the stent, such that the monofilament becomes embedded in the grooves.

32 Claims, 7 Drawing Sheets

U.S. PATENT DOCUMENTS

| | | | |
|---|---|---|---|
| 6,287,628 B1 | 9/2001 | Hossainy et al. | 427/2.3 |
| 6,355,063 B1 * | 3/2002 | Calcote | 623/1.42 |
| 6,379,381 B1 * | 4/2002 | Hossainy et al. | 623/1.42 |
| 6,551,353 B1 * | 4/2003 | Baker et al. | 623/1.42 |
| 2002/0004679 A1 * | 1/2002 | Eury et al. | 623/1.15 |
| 2002/0038145 A1 * | 3/2002 | Jang | 623/1.15 |
| 2003/0120331 A1 * | 6/2003 | Chobotov et al. | 623/1.13 |

FOREIGN PATENT DOCUMENTS

| | | |
|---|---|---|
| EP | 0 875 218 A2 | 4/1998 |
| JP | 11299901 | 11/1999 |
| WO | WO 90/01969 | 3/1990 |
| WO | WO 98/23228 | 6/1998 |
| WO | WO 99/16386 | 4/1999 |

* cited by examiner

IMPLANTABLE DRUG DELIVERY PROSTHESIS

BACKGROUND OF THE INVENTION

1. Field of the Invention

The present invention relates to a medical device for delivering a substance to a vascular lumen. More specifically, the present invention relates to a vascular stent capable of delivering a therapeutic substance.

2. Related Art

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the arterial lumen. The balloon is then deflated to a smaller profile to allow the catheter to be withdrawn from the patient's vasculature.

In treating the damaged vasculature tissue and to deter thrombosis and restenosis, therapeutic substances are commonly administered to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively.

Systemic administration of such therapeutic substances in sufficient amounts to supply an efficacious concentration to the local treatment site often produces adverse or toxic side effects for the patient. Accordingly, local delivery is a preferred method of treatment since smaller total levels of medication are administered and concentrated at a specific treatment site. Local delivery thus produces fewer side effects and achieves more effective results.

A common technique for local delivery of therapeutic substances employs medicated stents. For example, a metallic stent can be coated with a polymeric material which, in turn, is impregnated with a therapeutic substance or a combination of substances. Once the stent is implanted within a cardiovascular system lumen, the drug or drugs are released from the polymer for the treatment of the local tissues. What is needed is a stent design with improved mechanical functionality and drug delivery capabilities.

SUMMARY

The present invention provides an apparatus and associated method for delivering a therapeutic substance to a vascular lumen. In accordance with one aspect of the present invention, an implantable prosthesis, such as a stent, has grooves or trenches formed thereon. The grooves can be created using either lazing or selective mechanical/chemical etching techniques. The grooves are formed on specific regions of the stent struts, such as the connecting elements (i.e., links) or connecting arm elements (i.e., arms) to increase the flexibility of the stent. For example, by forming groove patterns on the arm elements of the stent, the bending/deflecting angle of the stent can be increased. Advantageously, since the arm elements tend to inherently oppose stent/balloon expansion, lower balloon expansion pressures can be used to extend the grooved arm elements, which can reduce or prevent injury to the vascular lumen. The increased stent flexibility can also facilitate the navigation of the stent through otherwise inaccessible or tortuous pathways, which lead to lesion sites.

In accordance with another aspect of the invention, the grooves can provide a therapeutic material carrying capability for treating intravascular ailments, such as restenosis and thrombosis. The therapeutic material loading of the grooves can be accomplished in several ways. For example, as described in greater detail below, a pure therapeutic material or a pre-mixed material with a polymer solution, which enhances the adhesion properties of the material, may be deposited directly into the grooves using conventional spray or modified dip techniques.

In another example, a microextruded monofilament therapeutic material can be embedded in the grooves. The monofilament generally resembles a string, which can be wound around the outside of the stent, so that the monofilament rests in the grooves. The monofilament therapeutic material becomes embedded in the grooves or is held in the grooves using an adhesive substance. Cutting, lazing, heating and the like can remove portions of the monofilament, which lay outside of the grooves, such that only the portion of the monofilament within the groove remains on the stent. Optionally, a top or barrier coating may be applied over the therapeutic monofilament embedded grooves to create a controllable release rate barrier.

Advantageously, the grooved stent can be deployed within the human vasculature with little or no significant loss of the therapeutic substance from the stent during delivery and expansion of the stent. The monofilament structure also provides for increased control of the release rate of the therapeutic substance from the stent.

In accordance with yet another aspect of the invention, an implantable prosthesis is provided including a tubular body structure including support elements separated by gaps; grooves disposed in said support elements; and a string strong enough to be circumferentially wrapped exclusively around the outer perimeter of said body structure of said implantable prostheses, said string being disposed in said grooves of at least some of said support elements such that said grooves act as guides for allowing said string to be circumferentially supported by said body structure, and wherein said string extends across said gaps between said support elements when circumferentially supported by said body structure.

Uses, advantages, and variations of the present invention will be apparent to one of ordinary skill in the art upon reading this disclosure and accompanying drawings.

Figure 1:
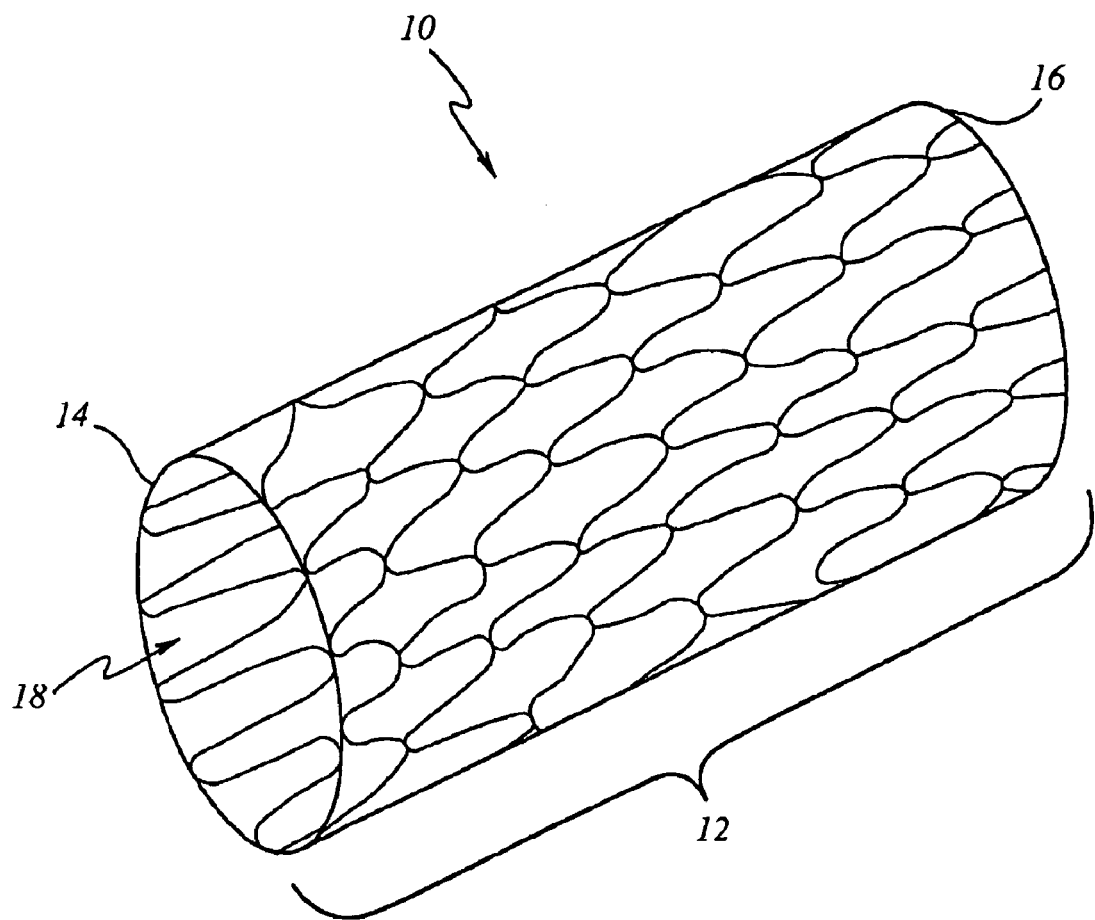
FIG. 1 is a simplified perspective view of a typical intraluminal prosthesis in accordance with an embodiment of the present invention.

The features of the described embodiments are specifically set forth in the appended claims. However, embodiments relating to both structure and method are best understood by referring to the following description and accompanying drawings, in which similar parts are identified by like reference numerals.

DETAILED DESCRIPTION

Stent deployment can result in early thrombus deposition and acute inflammation, granulation tissue development, and ultimately smooth muscle cell proliferation and extracellular matrix synthesis. The severity of arterial injury during stent placement correlates with increased inflammation in late neointimal growth. The progression of intimal thickening with time after experimental stent-induced vascular injury and clinical stent placement is well characterized. Experimental and clinical studies of endovascular stenting have demonstrated a complex network of vascular responses including thrombosis, neointimal hyperplasia, and inflammation. An implantable prosthesis can deliver a therapeutic substance designed to treat the various vascular responses to injury.

Referring now to the drawings, wherein similar parts are identified by like reference numerals, FIG. 1 illustrates a typical implantable prosthesis 10. Implantable prosthesis 10 includes a body structure 12 defined by an elongated tubular body having a first end 14, a second end 16, and a hollow lumen 18 extending therebetween. In one embodiment, implantable prosthesis 10 is an implantable stent. A typical implantable stent may take many shapes and forms and be of a variety of lengths. For example, the implantable stent may be a cylindrical tube that has had a pattern of rings and connecting elements formed thereon either, for example, by laser cutting, cutting or etching. The rings and connecting elements of the stent may be of a variety of thickness and lengths. Typically, an implantable stent can range in length from about 5 mm to about 50 mm. The actual physical dimensions of the implantable stent are dependent on the application.

Generally, an implantable stent is deployed in a physiological lumen from a radially compressed configuration into a radially expanded configuration which allows the stent to contact and support the physiological lumen. The stent is deformable such that it can be made to be radially self-expanding or expandable by the use of an expansion device. The self-expanding stent can be made from a resilient springy material while the device expandable stent can be made from a material which is plastically deformable. A plastically deformable stent can be implanted during an angioplasty procedure by using a balloon catheter. The deformable stent radially expands as the balloon is inflated, forcing the stent into contact with the interior of the physiological lumen thereby forming a supporting relationship with the lumen walls.

In accordance with one embodiment, implantable prosthesis 10 provides for delivery of a substance, such as a therapeutic substance or a combination of therapeutic substances, to a desired area of a vascular lumen in order to treat a localized area of the vascular lumen. It is contemplated that implantable prosthesis 10 has applicability for use with any biological or physiological lumen, for example, blood vessels, urinary tract lumen, intestinal tract lumen, kidney ducts, wind pipes, the vas deferens, ducts of the gallbladder, prostate gland, trachea, bronchus, liver and the like.

Figure 2:
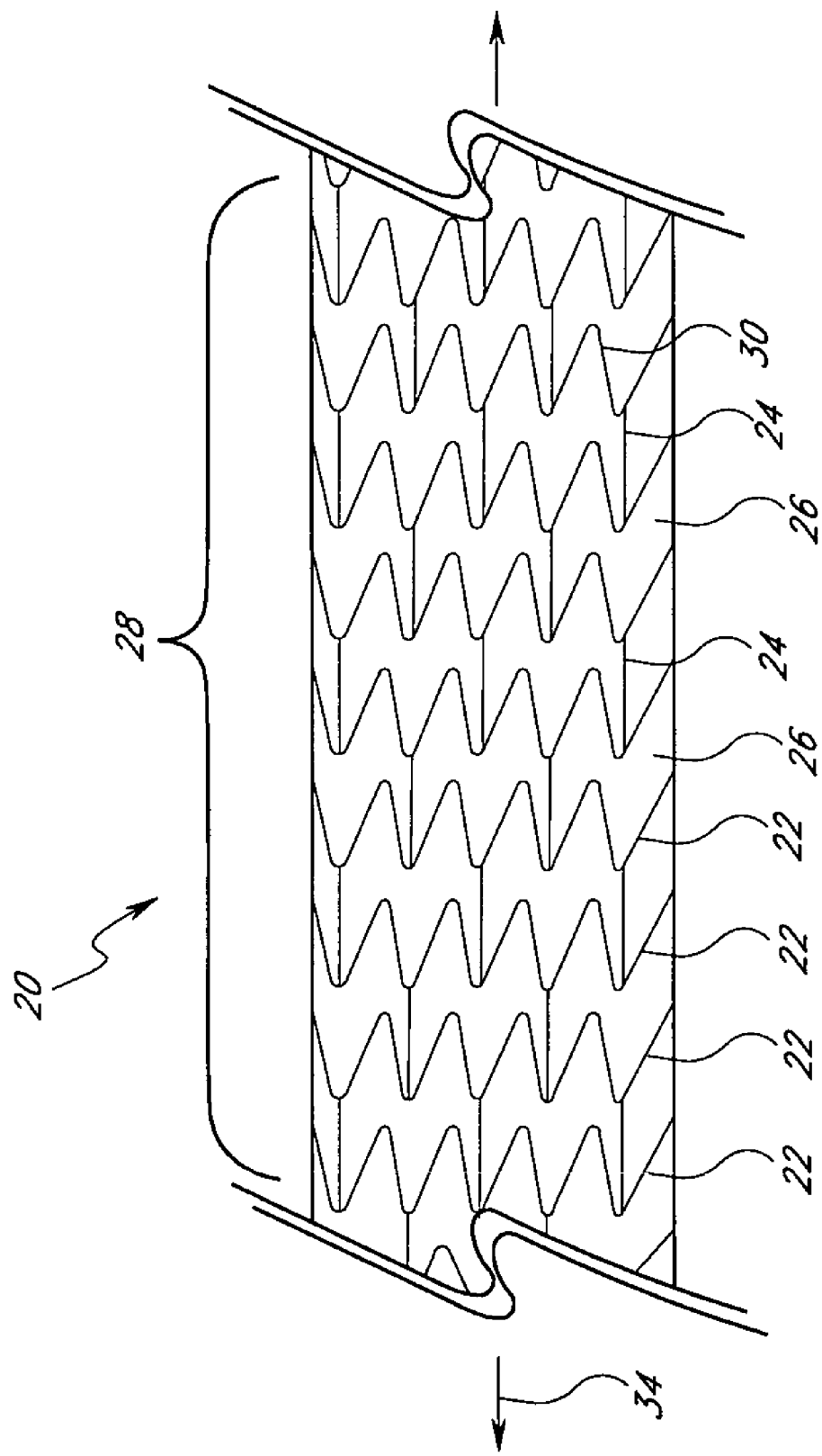
FIG. 2 is a simplified side view of a portion of an intraluminal prosthesis, the body of the prosthesis being defined by cylindrical elements engaged to one another by connecting elements.

As illustrated FIG. 2, in one embodiment, stent 20 can include a plurality of arm elements 22 that are arranged in a configuration that is connected to form a continuous ring or cylinder. The plurality of cylindrical arm elements 22 are radially expandable, disposed coaxially, and interconnected by connecting elements or links 24. Connecting elements 24 are disposed between adjacent cylindrical arm elements 22, leaving gaps or lateral openings 26 between adjacent cylindrical arm elements 22. Although the arm elements 22 are illustratively shown in the form of cylinders or rings connected axially and displaced in-parallel, other configurations, such as helices, coils, or braids, and other connections may be used. Arm elements 22 and connecting elements 24 define a tubular stent body 28 having a lumen contacting surface 30. Lumen contacting surface 30 includes the outwardly exposed surface portions of arm elements 22 and connecting elements 24.

Figure 3:
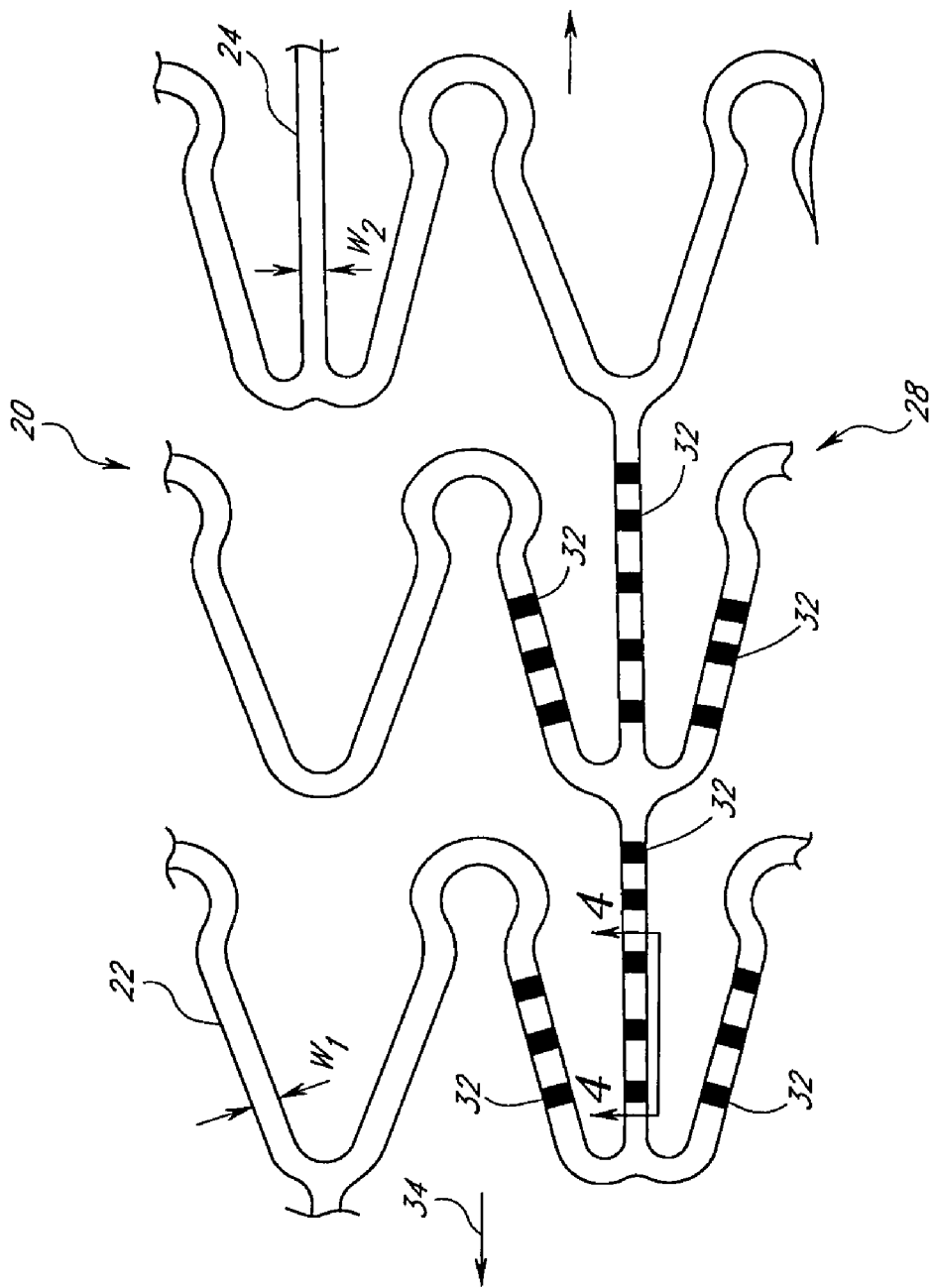
FIG. 3 is a close-up view of a portion of the intraluminal prosthesis of FIG. 2.

FIG. 3 is a close-up view of a portion of stent 20. Arm elements 22 have any suitable width $W_1$, typically in a range of width $W_1$ from about 0.05 mm to about 0.2 mm. A common width $W_1$ is about 0.08 mm. Connecting elements 24 have any suitable width $W_2$, typically in a range of width $W_2$ from about 0.05 mm to about 0.2 mm. A common width $W_2$ is about 0.12 mm. Additionally, arm elements 22 and connecting elements 24 have any suitable thickness, typically a thickness in a range from about 0.05 mm to about 0.2 mm. A common thickness T (FIG. 4) is about 0.12 mm. A specific choice of width and thickness depends on the anatomy and size of the target lumen. Thus, the size of the stent can vary according to intended procedure, anatomy, and usage.

Arm elements 22 and connecting elements 24 are typically fabricated from a metallic material or an alloy, such as stainless steel (e.g., 316L), MP35N, MP20N, tantalum, nickel-titanium alloy (commercially available as Nitinol™), platinum-iridium alloy, gold, magnesium, or combinations of alloys. MP35N and MP20N are trade names for alloys of cobalt, nickel, chromium and molybdenum available from standard Press Steel Co., Jenkintown, Pa. MP35N has a nominal composition of 35% cobalt, 35% nickel, 20% chromium, and 10% molybdenum. MP20N has a nominal composition of 50% cobalt, 20% nickel, 20% chromium, and 10% molybdenum.

As illustrated in FIG. 3, a single groove or channel 32 or plurality of grooves or channels 32 are formed as an open ended trench or trenches into arm elements 22 and/or connecting elements 24. In one embodiment, channels 32 are formed or cut across arm element 22 and/or connecting element 24, such that channels 32 are formed substantially perpendicular to a central axis 34 of stent 20, when stent 20 is in a collapsed configuration. It should be understood that as stent 20 expands, grooves 32 may change angle relative to central axis 34.

Grooves 32 can be formed by any well-known method of cutting or removing material, for example, by exposing arm elements 22 and/or connecting elements 24 to an energy discharge from a laser, such as a YAG laser or excimer laser. Alternative methods of forming grooves 32 include physical or chemical etching techniques. Techniques of laser fabrication or etching to form grooves 32 are well-known to one of ordinary skill in the art. Grooves 32 can be formed in virtually any stent structure and not merely the above-described structure.

The location or placement of grooves 32 on arm elements 22 and connecting elements 24 can vary according to the intended usage and application of stent 20. In one example, grooves 32 are evenly distributed over body 28 and have an equal volume so that the tissue in contact with stent 20 receives an equal distribution of a therapeutic substance.

Figure 4:
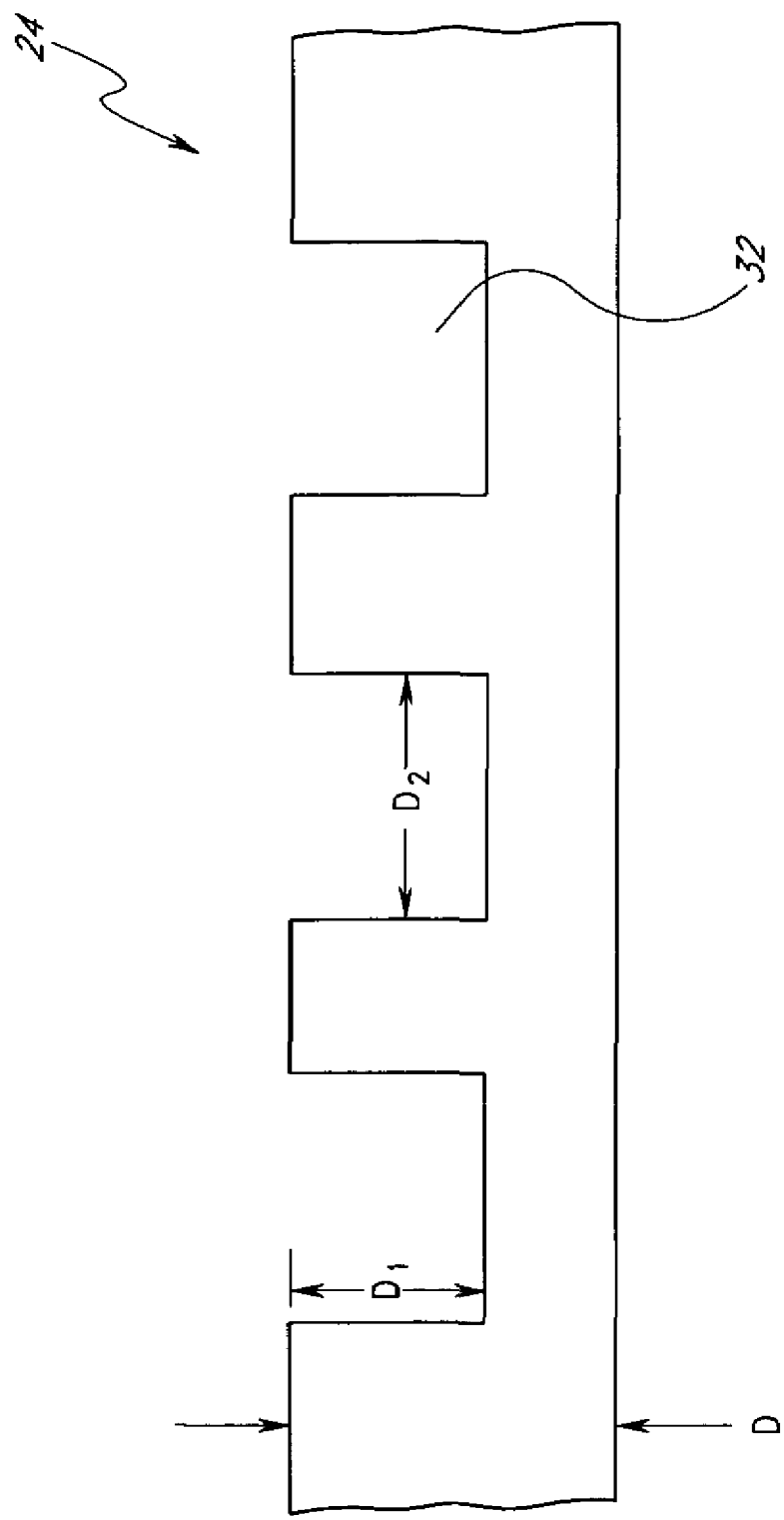
FIG. 4 is a cross sectional view along the line 4—4 of FIG. 3.

Grooves 32 can be formed to any suitable open-ended geometrical configuration, for example, a rectangular channel, which can have any preselected depth and size. As illustrated in FIG. 4, depth $D_1$ of groove 32 can be varied in proportion to the thickness T of connecting element 24 or arm element 22 depending on the clinical purpose and usage. In one embodiment, a suitable groove or channel depth $D_1$ has a range from about 10% to about 90% of thickness T. Typically, a depth not greater than about 50% of thickness T is most suitable. The specific depth $D_1$ of groove 32 depends on the amount of therapeutic substance that is to be deposited. In one example of stent 20 carrying a radioactive isotope, depth $D_1$ is typically about 10% to about 80% of thickness T. A more specific suitable depth is not greater than about 30% of thickness T. In another example, stent 20 carrying a radiopaque material, a suitable groove or channel 32 depth $D_1$ has a range from about 10% to about 90% of thickness T. Typically, a depth not greater than about 65% is most suitable. The upper limit of depth $D_1$ varies depending on the material characteristics, such as the hardness of the structural material used in stent 20.

Referring again to FIG. 4, groove 32 can have a breadth $D_2$, which can range from about 0.03 mm to about 0.18 mm, although the breadth $D_2$ is usually not greater than about 0.13 mm. The specific breadth $D_2$ depends on the application and purpose of the grooves 32. The upper limit of the breadth $D_2$ varies depending on the material characteristics of stent 20, such as the hardness of the structural material used in stent 20.

Although grooves 32 have been illustrated in FIG. 4 as having a substantially rectangular cross-section, it is anticipated that the actual shape of groove 32 can vary. For example, groove 32 may have a circular cross-section (cylindrical groove) having a diameter dependent on the application and purpose of the groove. Other grooves may be formed with triangular, oval, and other similar geometry.

Referring again to FIG. 3, grooves 32 are substantially aligned in axially displaced rows of grooves 32, where each row extends across stent 20 nearly perpendicular to axis 34. In one embodiment, for a given width $W_1$ or $W_2$, the depth $D_1$ and breadth $D_2$ (i.e., the volume) of each groove 32 in a row of grooves 32 on stent 20 can vary relative to other grooves in other rows of grooves 32. In one example, the manufacturer selectively controls the volume of grooves in a row on different positions of body 28, either selectively varying the volume between rows or making the volume consistent throughout body 28. For some applications, consistent groove volume provides evenly distributed therapeutic material delivery throughout stent 20 and results in consistent application of the therapeutic substance to the tissues in contact with surface 30 of stent 20.

In some embodiments, the therapeutic substance or agent, can include antineoplastics, anti-inflammatory substances, antiplatelets, anticoagulants, fibrinolytics, thrombin inhibitors, antimitotics, and antiproliferatives. Examples of antineoplastics include paclitaxel and docetaxel. Examples of antiplatelets, anticoagulants, fibrinolytics, and thrombin inhibitors include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen), and 7E-3B® (an antiplatelet drug from Centocore). Examples of suitable antimitotic agents include methotrexate, azathioprine, vincristine, vinblastine, flurouracil, adriamycin, mutamycin and actinomycin D. Examples of suitable cytostatic or antiproliferative agents include angiopeptin (a somatostatin analogue from Ibsen), angiotensin converting enzyme inhibitors such as Captopril® (available from Squibb), Cilazapril® (available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alphainterferon, genetically engineered epithelial cells, and dexamethasone.

While the listed therapeutic substances or agents are well known for preventative and therapeutic utility, the substances are listed by way of example and are not meant to be limiting. Other therapeutic substances which are currently available or that may be developed in the future are equally applicable. The treatment of patients using the above mentioned medicines is well-known to those of ordinary skill in the art.

In other embodiments, the therapeutic material can be a radioactive isotope for stent usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$).

Figure 5:
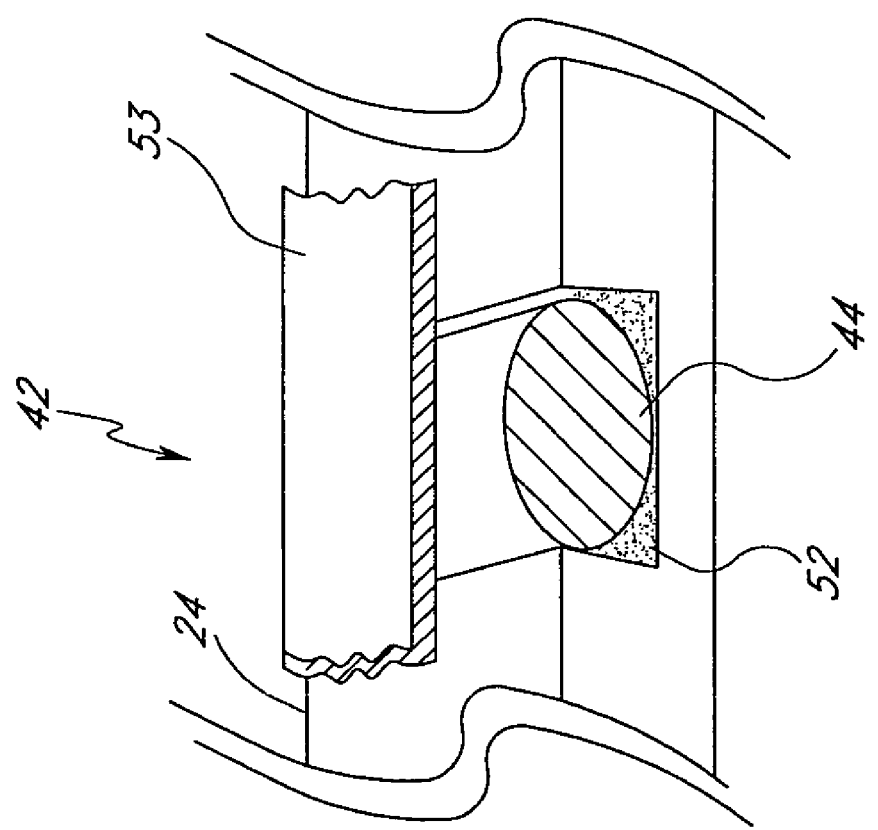
FIG. 5 is a partial close-up view of a groove loaded with a substance in accordance with one embodiment of the invention.
Figure 6:
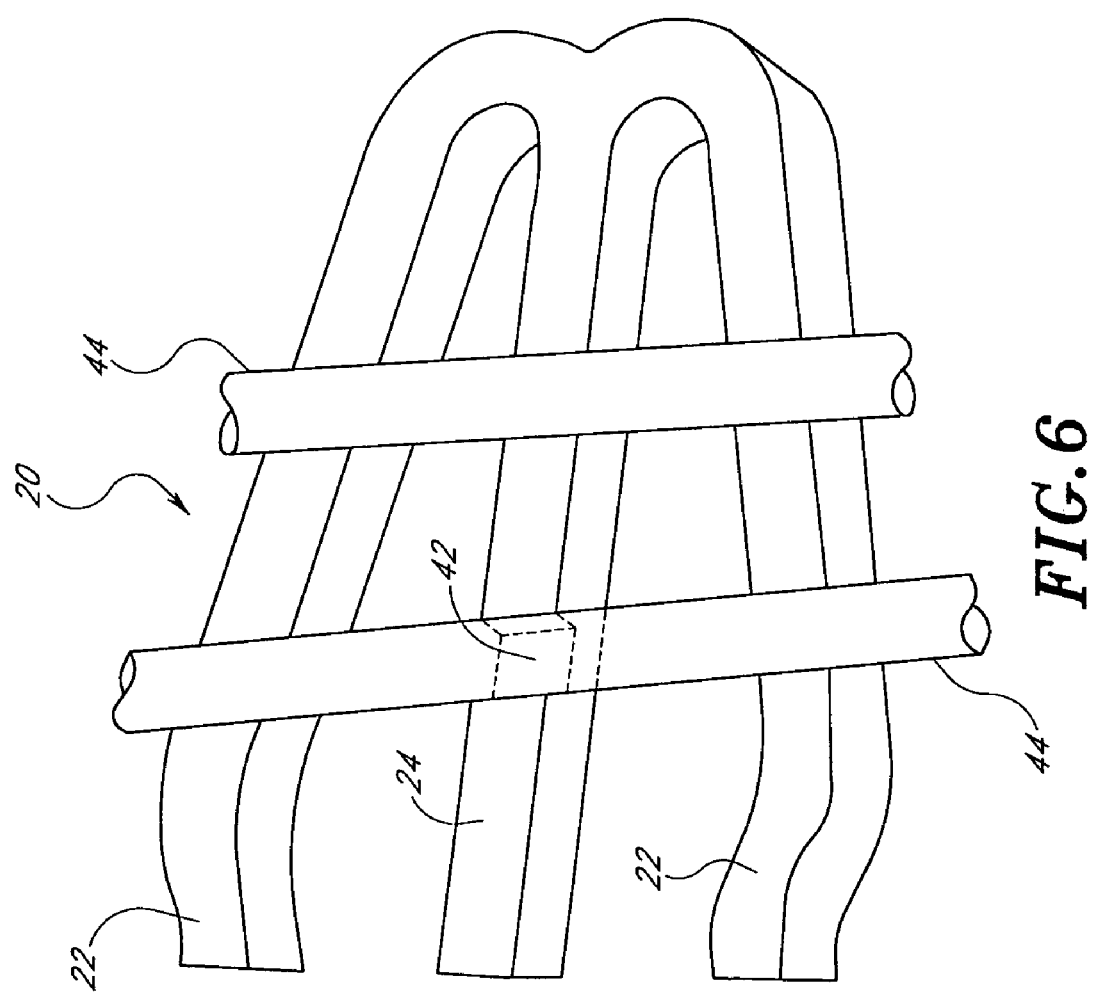
FIG. 6 is a simplified illustration of an implantable prosthesis.

FIG. 5 and FIG. 6 illustrate an embodiment for therapeutic substance loading in accordance with the present invention. In this embodiment, the therapeutic material can be dissolved or otherwise embedded into a polymer material, which is microextruded into a monofilament 44. Monofilament 44 is subsequently loaded onto stent 20.

Figure 7:
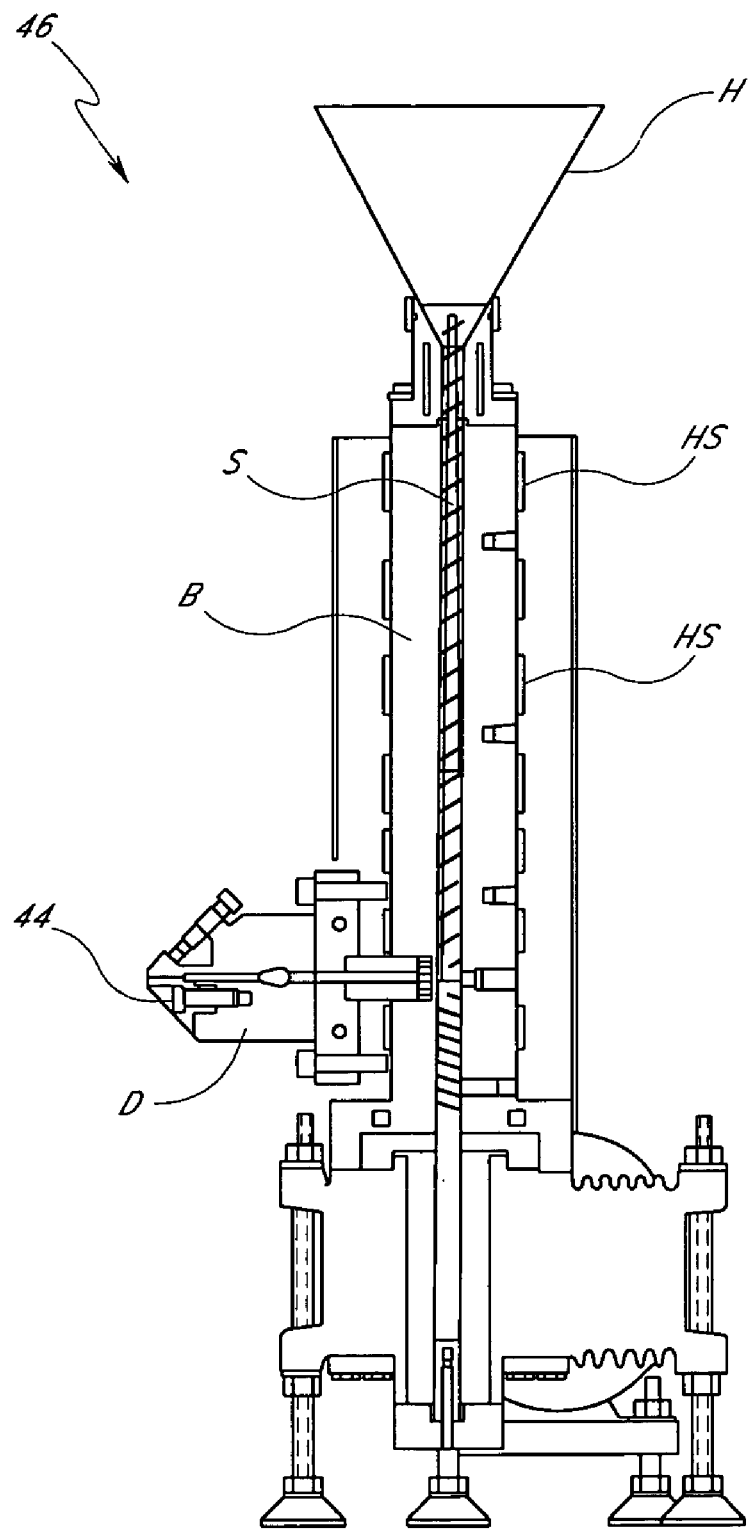
FIG. 7 is an illustration of a microextruder.

Monofilament 44 can be formed using any conventional microextrusion extruder, for example, the microextruder of the type illustrated in FIG. 7, available commercially from RANDCASTLE Extrusion Systems, Inc., of Cedar Grove, N.J. In this example, extruder 46 includes an extrusion screw S, which is driven from a drive end located at the upstream end of extrusion screw S. Hopper pellets of a polymeric material, as described below, are introduced into the hopper barrel H within which extrusion screw S is rotationally mounted. The therapeutic material can be added into hopper H to mix with the hopper pellets. Therapeutic parameters such as the concentration of the therapeutic substance in monofilament 44 and dosages depend on the duration of local release, the cumulative amount of release, and desired rate of release. Correlation and interrelation between the therapeutic parameters are well-known to one having ordinary skill in the art and are simply calculated. For example, polymer pellets of polyuethene can be mixed at a ratio of 10–30% of dexamethasone.

The hopper pellets and therapeutic substance are conveyed together downstream through barrel B and melted into molten polymer using heaters HS. It should be understood that in selecting both the polymer and therapeutic substance, the melting point of the polymer and the degradation temperature of the therapeutic substance should correlate such that the stability of the therapeutic substance is maintained. For example, the therapeutic substances b-estradiol, Vincristine and Colchicine, have degradation temperature limits of about 200° C., 60° C. and 200° C., respectively. These substances should be used with polymers having melting point temperatures lower than their degradation temperatures. For example, ethylene vinyl alcohol, which has a melting point of 160° C. and low-density polyethylene, which has a melting point of 120° C., may be used with b-estradiol and Colchicine, while polyethylene glycol, which has a melting point of about 50° C., may be used with Vincristine. Correlation and interrelation between the therapeutic temperature parameters and the polymer temperature parameters are well-known to one having ordinary skill in the art and are simply planned.

The medicated melted polymer is discharged to an extrusion die D to form monofilament 44. The general dimensions of monofilament 44 are such that they substantially conform to the dimensions of grooves 32 (FIG. 3).

In one embodiment, monofilament 44 is processed to resemble a "string." As shown in FIG. 6, string monofilament 44 can be wrapped around the outside surface 30 of stent 20, such that monofilament 44 comes to rest in the grooves, such as groove 42 (shown in phantom). In one embodiment, a liquid polymer 52 (FIG. 5) may be used to attach certain areas of monofilament 44 to stent 20. Liquid polymer 52 may be, for example, a medical adhesive, such as those available from Master Bond, Inc. of Hackensack, N. J. In another embodiment, monofilament 44 can be sized such that monofilament 44 is force fit into the grooves.

Once monofilament 44 is disposed within the grooves, a laser can be used to cut and remove portions of monofilament 44 which are not held within the grooves. Alternatively, a heat source can be brought proximate to stent 20, such that portions of monofilament 44 that are not held within the grooves can melt or dissolve away. As illustrated in FIG. 5, monofilament 44 remains in channel 42 until prosthesis deployment and expansion. The expanded prosthesis engages the wall of the anatomical lumen and the therapeutic substance is absorbed into the tissue of the walls of the body lumen that are in contact with prosthesis surface 30 (FIG. 2).

In one embodiment, stent 20 can be coated with a therapeutic substance in addition to having a therapeutic substance deposited in channels 32. The therapeutic substance is a substance that is capable of absorbing or attaching to the prosthesis surface. For example, highly suitable therapeutic substances for a stainless steel prosthesis include paclitaxel and dexamethasone, substances that easily attach to a metallic substrate.

In another embodiment, a polymeric coating 53 (FIG. 5) can be formed on the surface of the prosthesis covering the channel. In this embodiment, coating 53 covers channel 42 containing the deposited therapeutic substance monofilament 44. Polymeric coating 53 forms a membrane that reduces the rate of release of a therapeutic substance from the channel.

In the embodiments, polymeric monofilament 44 is suitably bio-compatible, non-toxic, non-inflammatory, chemically inert, and substantially non-immunogenic. Monofilament 44 can be typically either bioabsorbable or biostable. A bioabsorbable polymer bio-degrades or breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable biodegradable materials include but are not limited to polycaprolactone(PCL), poly-D,L-lactic acid(DL-PLA), poly-L-lactic acid(L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphospho-ester urethane, poly (amino acids), cyanoacrylates, poly (trimethylene carbonate), poly(iminocarbonate), copoly (ether-esters), polyalkylene oxalates, polyphosphazenes, polyiminocarbonates, and aliphatic polycarbonates. Examples of biostable polymers include Parylene®, Parylast® polyurethane (for example, segmented polyurethanes such as Biospan®), polyethylene, polyethylene terephthalate, ethylene vinyl acetate, silicone and polyethylene oxide. Biomolecules such as heparin, fibrin, fibrinogen, cellulose, starch, and collagen represent other substances which can be used to coat, or alternatively can be embedded into the biostable polymer.

While particular embodiments of the present invention have been shown and described, it will be obvious to those having ordinary skill in the art that changes and modifications can be made without departing from this invention in its broader aspects. For example, although a particular stent shape with particular arm elements and connecting elements is described herein, those having ordinary skill in the art would recognize that other stent shapes could be used as well, including a tubular stent. Those having ordinary skill in the art would also recognize that although coronary applications are described herein, Applicants' implantable prosthesis can be any type of stent, including peripheral or neurological stents. Therefore, the appended claims are to encompass within their scope all such changes and modifications as fall within the scope of the invention.

What is claimed is:

1. An implantable prosthesis, comprising:
    a body structure having an outer surface for contacting a surface of a lumen;
    a plurality of grooves disposed on said outer surface of said body structure of said implantable prosthesis; and
    a continuous string having a therapeutic substance, said string resting in a plurality of said grooves, wherein said string is capable of being wound around said body structure.

2. The implantable prosthesis of claim 1, wherein a depth of said grooves is equal to about 10% to 90% of a thickness of said body structure.

3. The implantable prosthesis of claim 1, wherein a depth of said grooves is not greater than about 65% of a thickness of said body structure.

4. The implantable prosthesis of claim 1, wherein said string comprises a polymer material.

5. The implantable prosthesis of claim 1, wherein said therapeutic substance comprises a substance selected from the group consisting of antineoplastic, antiplatelet, anticoagulant, fibrinolytic, antimitotic, thrombin inhibitor, antiinflammtory, and antiproliferative agents.

6. The implantable prosthesis of claim 1, wherein said therapeutic substance comprises a radioactive isotope.

7. The implantable prosthesis of claim 1, further comprising a barrier disposed on said outer surface of said body structure and on said string to reduce the rate at which said therapeutic substance is released.

8. The implantable prosthesis of claim 1, wherein said body structure comprises a radially expandable tubular structure.

9. The implantable prosthesis of claim 1, wherein said body structure includes arm elements joined by connecting elements.

10. The implantable prosthesis of claim 1, additionally including an adhesive material capable of bonding said string in said grooves.

11. The implantable prosthesis of claim 1, wherein a thickness of said string is generally equivalent to a width of said grooves so as to provide a tight fit between said string and said grooves.

12. The implantable prosthesis of claim 1, wherein a thickness of said string is generally equivalent to a depth of said grooves such that said string does not protrude out from said grooves.

13. The implantable prosthesis of claim 1, wherein said string is a monofilament.

14. The implantable prosthesis of claim 1, wherein said string is made at least in part from a polymeric material.

15. The implantable prosthesis of claim 1, wherein said string comprises a filament.

16. The implantable prosthesis of claim 1, wherein said string comprises an extruded filament.

17. The implantable prosthesis of claim 1, further comprising:
an adhesive material disposed on said body structure or on said string or both.

18. An implantable prosthesis, comprising:
tubular body structure including support elements separated by gaps;
grooves disposed in said support elements; and
a string including a therapeutic substance, said string strong enough to be circumferentially wrapped exclusively around the outer perimeter of said body structure of said implantable prosthesis, said string being disposed in said grooves of at least some of said support elements such that said grooves act as guides for allowing said string to be circumferentially supported by said body structure, and wherein said string extends across said gaps between said support elements when circumferentially supported by said body structure.

19. The implantable prosthesis of claim 18, wherein a depth of said grooves is equal to about 10% to 90% of a thickness of said support elements.

20. The implantable prosthesis of claim 18, wherein a depth of said grooves is not greater than about 65% of a thickness of said support elements.

21. The implantable prosthesis of claim 18, wherein said string comprises a polymer material.

22. The implantable prosthesis of claim 18, wherein said therapeutic substance comprises a substance selected from the group consisting of antineoplastic, antiplatelet, anticoagulant, fibrinolytic, antimitotic, thrombin inhibitor, antiinflammatory, and antiproliferative agents.

23. The implantable prosthesis of claim 18, wherein said therapeutic substance comprises a radioactive isotope.

24. The implantable prosthesis of claim 18, further comprising a barrier disposed on an outer surface of said body structure and on said string to reduce the rate at which said therapeutic substance is released.

25. The implantable prosthesis of claim 18, wherein said body structure comprises a radially expandable tubular structure.

26. The implantable prosthesis of claim 18, wherein said support elements comprise arm elements joined by connecting elements.

27. The implantable prosthesis of claim 18, additionally including an adhesive material capable of bonding said string in said grooves.

28. The implantable prosthesis of claim 18, wherein a thickness of said string is generally equivalent to a width of said grooves so as to provide a tight fit between said string and said grooves.

29. The implantable prosthesis of claim 18, wherein a thickness of said string is generally equivalent to a depth of said grooves such that said string does not protrude out from said grooves.

30. The implantable prosthesis of claim 18, wherein said string is a monofilament.

31. An implantable prosthesis, comprising:
a body structure including support elements separated by gaps;
grooves disposed in said support elements; and
a continuous string including a therapeutic substance, said string disposed in said grooves of at least some of said support elements such that said grooves act as guides for allowing said string to be supported by said body structure of said implantable prosthesis, wherein said string extends across said gaps between said support elements when supported by said body structure.

32. The implantable prosthesis of claim 31, wherein said implantable prosthesis is a stent.

* * * * *